United States Patent [19]

Barth et al.

[11] Patent Number: 4,499,089

[45] Date of Patent: Feb. 12, 1985

[54] 2-ALKYLTHIO-1-AMINOALKYL-2-PYRROLINE-3-CARBONITRILES, COMPOSITIONS AND USE

[75] Inventors: Hubert Barth, Emmendingen; Johannes Hartenstein, Stegen-Wittental; Gerhard Satzinger, Denzlingen; Edgar Fritschi, St. Peter; Volker Ganser, Freiburg; Horst-Dietmar Tauschel, Ettenheim; Günter Wolf, Freiburg, all of Fed. Rep. of Germany

[73] Assignee: Warner-Lambert Company, Morris Plains, N.J.

[21] Appl. No.: 608,828

[22] Filed: May 10, 1984

[30] Foreign Application Priority Data

May 14, 1983 [DE] Fed. Rep. of Germany ....... 3317653

[51] Int. Cl.$^3$ .................... A61K 31/40; A61K 31/54; C07D 417/06; C07D 207/277

[52] U.S. Cl. .................... 514/222; 514/232; 514/326; 514/333; 514/425; 544/58.5; 544/58.6; 544/58.7; 544/131; 544/141; 544/360; 544/364; 544/372; 546/193; 546/194; 546/205; 546/206; 546/208; 546/256; 546/281; 548/517; 548/524; 548/527; 548/546

[58] Field of Search .................... 544/58.5, 58.6, 58.7, 544/131, 141, 360, 364, 372; 546/193, 194, 205, 206, 208, 256, 281; 548/517, 524, 527, 546; 424/246, 248.52, 250, 263, 267, 274

[56] References Cited

FOREIGN PATENT DOCUMENTS 91045 10/1983 European Pat. Off. .

OTHER PUBLICATIONS

European Patent Application 0,091,045, Oct. 12, 1983, Barth et al.

Primary Examiner—Robert W. Ramsuer
Attorney, Agent, or Firm—Ronald A. Daignault

[57] ABSTRACT

2-Alkylthio-1-aminoalkyl-2-pyrroline-3-carbonitriles and pharmaceutically acceptable acid addition salts, processes for their preparation and formulation into pharmaceutical compositions as well as their activity as thrombocyte aggregation-inhibitors are described. The compounds are thus useful for the prophylaxis and therapy of thrombotic states.

15 Claims, No Drawings

2-ALKYLTHIO-1-AMINOALKYL-2-PYRROLINE-3-CARBONITRILES, COMPOSITIONS AND USE

SUMMARY OF THE INVENTION

The invention concerns 2-alkylthio-1-aminoalkyl-2-pyrroline-3-carbonitriles of the general formula I

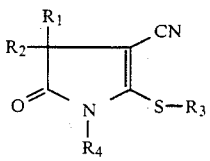

in which $R_1$ and $R_2$ are the same or different and signify an optionally substituted aromatic ring, $R_3$ signifies a straight or branched chain hydrocarbon group of one to four carbon atoms, preferably a methyl, ethyl, n-propyl or isopropyl group, $R_4$ signifies an aminoalkyl group of the general formula II

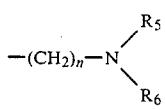

in which n is equal to two or three and $R_5$ and $R_6$ are the same or different and individually signify hydrogen, a straight or branched chain alkyl group of one to four carbon atoms or, together with the nitrogen atom to which they are attached, an signify a ring with possible further heteroatoms, as well as their pharmaceutically acceptable acid-addition salts. Compounds of general formula I are preferred in with $R_1$ and $R_2$ are the same and signify a phenyl or pyridyl ring, $R_3$ signifies a straight or branched chain $C_{1-3}$ alkyl group and $R_4$ signifies an aminoalkyl group of general formula II, in which n is equal to two or three, and $R_5$ and $R_6$ are the same or different and signify hydrogen, a methyl, ethyl, propyl or isopropyl radical or, together with the nitrogen atom to which they are attached, can represent a pyrrolidino, piperidino, morpholino or piperazino group, as well as their pharmaceutically acceptable acid addition salts. Furthermore, there are claimed processes for their preparation and their use in the prophylaxis and therapy of thrombotic states and pharmaceutical preparations containing at least one compound of general formula I.

DETAILED DESCRIPTION

The subject of the invention are 2-alkylthio-1-aminoalkyl-2-pyrroline-3-carbonitriles of the general formula I

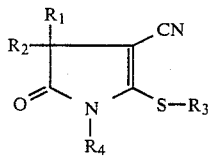

in with $R_1$ and $R_2$ are the same or different and signify an optionally substituted aromatic ring, $R_3$ signifies a straight or branched chain hydrocarbon of one to four carbon atoms, preferably a methyl, ethyl, n-propyl or isopropyl group, $R_4$ signifies an aminoalkyl group of the general formula II

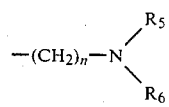

in which n is equal to two or three, and $R_5$ and $R_6$ are the same or different and individually signify hydrogen, a straight or branched chain alkyl group of one to four carbon atoms or, together with the nitrogen atom to which they are attached, a ring with possibly further heteroatoms, as well as their pharmaceutically acceptable acid-addition salts.

An optionally substituted aromatic ring includes phenyl α- or β-naphthyl, 2- or 3-thienyl, 2- or 3-furanyl or 2-, 3- or 4-pyridyl or phenyl, α- ar β-naphthyl substituted by alkyl of one to four carbon atoms, alkoxy of one to four carbon atoms, halogen, trifluoromethyl, nitro, amino, alkyl or dialkylamino of one to four carbon atoms, or substituted thienyl, furanyl or pyridyl wherein the substituent is alkyl of one to four carbon atoms.

Halogen atoms are those of the periodic group of elements and preferably fluorine, chlorine or bromine.

When $R_5$ and $R_6$ are taken together with the nitrogen atom to form a ring with possibly further heteroatoms, there are included by way of example 5- or 6-membered rings which form groups such as pyrrolidino, piperidino, piperazino, morpholino or thiamorpholino.

Compounds of general formula I are preferred in which $R_1$ and $R_2$ signify a phenyl, a dimethylaminophenyl or a pyridyl ring, $R_3$ signifies a straight or branched chain $C_{1-3}$ alkyl group and $R_4$ an aminoalkyl group of the general formula II

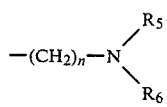

in which n is equal to two or three, and $R_5$ and $R_6$ are the same or different and signify hydrogen, a methyl, ethyl, propyl or isopropyl radical or, together with the nitrogen to which they are attached, signify a pyrrolidino, piperidino, morpholino or piperazino group, as well as their pharmaceutically acceptable acid addition salts.

The compounds according to formula I are prepared in that one reacts a 2-pyrroline-3-carbonitrile of the general formula III

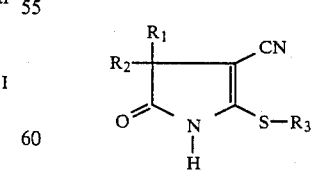

in which $R_1$ and $R_2$ are the same or different and stand for an optionally substituted aromatic ring and $R_3$ stands for a straight or branched chain hydrocarbon group of one to four carbon atoms, in a suitable solvent in the presence of a strong base with a compound of the general formula IV

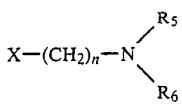

in which n is equal to two or three, $R_5$ and $R_6$ which may be the same or different are a straight or branched chain alkyl group of one to four carbon atoms or together with the nitrogen atom to which they are attached form a ring possibly containing further hetero atoms, whereby one of the radicals $R_5$ or $R_6$ may also be a hydrogen atom and X represents a halogen atom, and subsequently possibly converts the compound obtained of general formula I into its pharmacologically acceptable acid addition salts.

As solvents, there come into question polar protic or dipolar aprotic solvents. Lower alcohols, such as, e.g., methanol or ethanol, or cyclic ethers such as, e.g., dioxan or tetrahydrofuran are preferred. The alkylation reaction requires the presence of strong bases. Preferred as bases in the case of working in polar protic solvents are sodium methylate and sodium ethylate, in the case of working in dipolar aprotic solvents sodium hydride. The reaction times amount to between 2 to 24 hours.

The alkylation agents of the general formula IV used for the alkylation are preferably used in the form of their hydrochlorides or -bromides. In this case, for the alkylation one uses 2 mole equivalents of base. In the case of the use of dioxan or tetrahydrofuran as solvent and sodium hydride as base, for the alkylation one preferably uses the free base of general formula IV.

The reaction products of general formula I, after filtration from precipitated alkali metal halide, crystallize directly from the filtrate or are obtained, after concentration of the reaction mixture and not miscible with water, such as, e.g., methylene chloride, and water, after evaporation of the organic phase and crystallization from a suitable solvent.

Bases which are difficult to crystallize are converted into suitable pharmaceutically acceptable acid-addition salts. As such, there come into question the salts or organic and inorganic acids, such as, e.g., hydrochloric acid, sulphuric acid, phosphoric acid, hydrobromic acid, acetic acid, maleic acid, fumaric acid, oxalic acid, succinic acid. The salts are prepared in per se known manner by reaction of the base with corresponding organic and inorganic acids.

Another process for the preparation of compounds according to the invention consists in that one reacts 2-pyrroline-3-carbonitriles of the general formula III

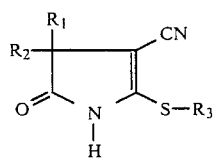

in which $R_1$ and $R_2$ are the same or different and stand for a phenyl, substituted phenyl or pyridyl radical and $R_3$ stands for a straight or branched chain lower hydrocarbon group, in a suitable solvent in the presence of a strong base with a compound of the general formula V $$X-(CH_2)_n-X' \qquad V$$

in which n is equal to two or three and X and X' which may be the same or different stand for a halogen atom, and reacts the compounds obtained of the general formula VI

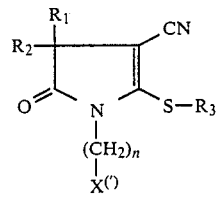

in a suitable solvent either with an alkylamine of the general formula VII

wherein $R_5$ and $R_6$ have the above mentioned meaning, to give compounds of general formula I or by decomposing a compound of the general formula VIII

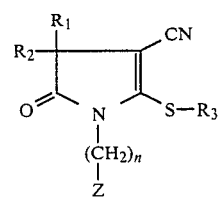

wherein $R_1$, $R_2$, $R_3$ and n have the above mentioned meaning and Z is an amino group provided with a protecting group, which may be split of by means of an acid in per se known manner with acids to give compounds of general formula I.

As solvents for the preparation of compounds of general formula VI, there are especially suitable dioxan or tetrahydrofuran. In this case, one uses sodium hydride as base and uses as alkylation agent of general formula V a tenfold excess. After the reaction, it is filtered off from precipitated alkali metal halide and the solvent, as well as the excess alkylation agent, is removed in a vacuum. The residue is crystallized from a suitable solvent.

The reaction of compounds of general formula VI with amines of general formula VII is preferably carried out in dioxan or ethanol in the presence of an excess of amine at room temperature. The reaction time amounts to 12 to 24 hours. After removal of the solvent, the reaction products are chromatographed on silica gel.

As compounds of general formula VIII there may be used such containing amino groups Z provided with protecting groups which are conventional in peptide chemistry, such as, e.g., the benzylidene-amino group, the phenyl-carbonyl-amino group, the hexamethylenetetraammonium cation or the triphenylmethyl-amino group. Processes of manufacturing such compounds are well known in the art (see, e.g., J. Org. Chem. 1983, 48, 24–31).

Compounds VIII with a hexamethylenetetrammonium cation may be obtained by reacting hexamethylenetetramine with a compound of the general formula VI in a polar solvent such as, e.g., chloroform.

The decomposition of the compounds of general formula VIII takes place with the use of mixtures of conc. hydrochloric acid and ethanol or of conc. hydrobromic acid and ethanol. After removal of the acid/alcohol mixture in a vacuum, the residue is chromatographed on silica gel and the desired fraction crystallized after evaporation. The compounds of general formula III serving as starting materials are described in published Federal Republic of Germany Patent Application No. 321259.7. The compounds of general formula I preparable according to the process of the invention are new and display valuable pharmacological properties. In particular, they display thrombocyte aggregation-inhibiting actions. Furthermore, the compounds according to the invention are antiphlogistic, antipyretic, antisecretory and ulcer-protective. The oral compatibility of the compounds is very good. A further subject of the invention is, accordingly, the use of compounds of general formula I in the prophylaxis and therapy of thrombotic states.

The compounds of general formula I according to the invention can be administered orally or parenterally as pharmaceutical compositions containing pharmaceutically acceptable carriers in liquid or solid form. As injection solution, water is especially used which contains the additives usual in the case of injection solutions, such as stabilizing agents, solubilizing agents or buffers.

Such additives are, e.g., tartrate and citrate buffers, ethanol, complex formers (such as ethylenediamine-tetraacetic acid and its nontoxic salts), as well as high molecular polymers (such as liquid polyethylene oxide) for viscosity regulation. Solid carrier materials are, e.g., starch, lactose, mannitol, methyl cellulose, talc, highly dispersed silicic acids, high molecular fatty acids (such as stearic acid), gelatine, agar-agar, calcium phosphate, magnesium stearate, animal and vegetable fats, solid high molecular polymers (such as polyethylene glycols); compositions suitable for oral administration can, if desired, contain additional flavoring and/or sweetening materials.

The following examples serve for the explanation of the invention.

EXAMPLE 1

2-Ethylthio-5-oxo-4,4-diphenyl-1-(2-piperidinoethyl)-2-pyrroline-3-carbonitrile hydrochloride (1)

One dissolves 1.38 g sodium in 200 ml abs. ethanol, adds 9.6 g 2-ethylthio-5-oxo-4,4-diphenyl-2-pyrroline-3-carbonitrile thereto and heats under reflux for 30 min., a solution of 5.5 g. N-(2-chloroethyl)-piperidine in 60 ml. ethanol and further boils for two hours. The reaction mixture is evaporated and the residue partitioned between ether and water. The ethereal phase is dried over sodium sulphate and finally mixed with ethereal hydrogen chloride solution. The precipitated deposit is filtered off with suction and crystallized from isopropanol.

Yield 10.5 g of colorless crystals of mp 210° C., decomp.

In analogous manner there are obtained:
1-(2-diethylaminoethyl)-2-ethylthio-5-oxo-4,4-diphenyl-2-pyrroline-3-carbonitrile hydrochloride (2), yield 73%, mp 187° C., decomp.
2-ethylthio-1-(3-dimethylaminopropyl)-5-oxo-4,4-diphenyl-2-pyrroline-3-carbonitrile hydrochloride (3), yield 46%, mp 188° C., decomp.
2-ethylthio-1-(3-dimethylaminoethyl)-5-oxo-4,4-diphenyl-2-pyrroline-3-carbonitrile (4), yield 38%, mp 128° C.
2-ethylthio-1-(3-morpholinopropyl)-5-oxo-4,4-diphenyl-2-pyrroline-3-carbonitrile (5), yield 53%, mp 97° C.

EXAMPLE 2

2-Isopropylthio-1-(3-dimethylaminopropyl)-5-oxo-4,4-diphenyl-2-pyrroline-3-carbonitrile (8)

A suspension of 10.0 g 2-isopropylthio-5-oxo-4,4-diphenyl-2-pyrroline-3-carbonitrile and 0.9 g sodium hydride (80%) in 150 ml dioxan is boiled for one hour, with stirring. Thereafter, one mixes with a further 0.9 g sodium hydride and 5.2 g dimethylaminopropyl chloride hydrochloride and boils further for 30 hours.

The reaction mixture is filtered, the filtrate is evaporated to dryness and the residue is chromatographed on silica gel with chloroform/methanol 10+1. One obtains 3.7 g of colorless crystals, mp 92° C.

EXAMPLE 3

1-(2-Diethylaminoethyl)-5-oxo-4,4-diphenyl-2-propylthio-2-pyrroline-3-carbonitrile (9)

A suspension of 10.0 g 5-oxo-4-4-diphenyl-2-propylthio-2-pyrroline-3-carbonitrile and 0.9 g sodium hydride (80%) in 200 ml dioxan is heated under reflux for one hour. Thereafter, one adds dropwise a solution of 5.8 g diethylaminoethyl chloride in 20 ml dioxan thereto and further boils under reflux for six hours. The reaction mixture is filtered, the filtrate is evaporated to dryness and the residue crystallized from isopropanol. Yield 8.6 g of colorless crystals of mp 55° C.

In analogous manner there are obtained:
1-(2-dimethylaminopropyl)-2-methylthio-5-oxo-4,4-diphenyl-2-pyrroline-3-carbonitrile (6), yield 76%, mp 106° C.
1-(2-diethylaminoethyl)-2-methylthio-5-oxo-4,4-diphenyl-2-pyrroline-3-carbonitrile (7), yield 50%, mp 86° C.
1-(2-diethylaminoethyl)-2-isopropylthio-5-oxo-4,4-diphenyl-2-pyrroline-3-carbonitrile (10), yield 56%, mp 66° C.
2-methylthio-1-(3-morpholinopropyl)-5-oxo-4,4-diphenyl-2-pyrroline-3-carbonitrile (11), yield 45%, mp 139° C.
2-methylthio-5-oxo-4,4-diphenyl-1-(3-piperidinopropyl)-2-pyrroline-3-carbonitrile (12), yield 50%, mp 124° C.
2-methylthio-5-oxo-4,4-diphenyl-1-(3-pyrrolidinoethyl)-2-pyrroline-3-carbonitrile (13), yield 43%, mp 97° C. 1-(2-diisopropylaminoethyl)-2-methylthio-5-oxo-4,4-diphenyl-2-pyrroline-3-carbonitrile (14), yield 40%, mp 98° C.
2-ethylthio-5-oxo-4,4-diphenyl-1-(3-piperidinopropyl)-2-pyrroline-3-carbonitrile oxalate (15), yield 60%, mp 199° C., decomp.
1-(3-diethylaminopropyl)-2-ethylthio-5-oxo-4,4-diphenyl-2-pyrroline-3-carbonitrile hydrochloride (16), yield 49%, mp 197° C., decomp.
1-(3-dimethylaminopropyl)-5-oxo-4,4-diphenyl-2-propylthio-2-pyrroline-3-carbonitrile hydrochloride (17), yield 29%, mp 178° C., decomp.

EXAMPLE 4

2-Ethylthio-5-oxo-1-(2-piperidinoethyl)-4,4-bis-(2-pyridyl-2-pyrroline-3-carbonitrile (18)

One dissolves 2.1 g sodium in 250 ml abs. ethanol, adds 14.1 g 2-ethylthio-5-oxo-4,4-bis-(2-pyridyl)-2-pyrroline-3-carbonitrile thereto and heats under reflux for ten minutes. One adds dropwise thereto a solution of 8.3 g. N-(2-chloroethyl)-piperidine hydrochloride in 80 ml ethanol and further boils for one hour. The reaction mixture is evaporated and the residue partitioned between methylene chloride and water. The organic phase is evaporated to dryness and the residue crystallized from ethanol. Yield 9.9 g of colorless crystals, mp 139° C.

In analogous manner there are obtained:
2-ethylthio-1-(3-dimethylaminopropyl)-5-oxo-4,4-bis-(2-pyridyl)-2-pyrroline-3-carbonitrile (20), yield 58%, mp 101° C.
1-(2-diethylaminoethyl)-2-ethylthio-5-oxo-4,4-bis-(2-pyridyl)-2-pyrroline-3-carbonitrile fumarate (19), yield 42%, mp 150° C.

EXAMPLE 5

1-(3-Aminopropyl)-2-ethylthio-5-oxo-4,4-diphenyl-2-pyrroline-3-carbonitrile hydrochloride (17a)

Variant A:

One dissolves 15.0 g 2-ethylthio-5-oxo-4,4-diphenyl-2-pyrroline-3-carbonitrile in 500 ml abs. dioxan, adds 1.4 g sodium hydride (80%) in white oil) thereto and boils under reflux for one hour. One allows to cool somewhat, adds 100.0 g 1,3-dibromopropane thereto and further boils for 48 hours. Thereafter, the reaction mixture is filtered, the solvent and the excess dibromopropane are distilled off under water pump vacuum and the residue is triturated with diisopropyl ether. One obtains 14.0 g 1-(3-bromopropyl)-2-ethylthio-5-oxo-4,4-diphenyl-2-pyrroline-3-carbonitrile of mp 97° C.

8.7 g 1-(3-Bromopropyl)-2-ethylthio-5-oxo-4,4-diphenyl-2-pyrroline-3-carbonitrile and 2.8 g urotropine are stirred for eight days at room temperature in 60 ml chloroform. The resultant precipitate is filtered off, washed out with some chloroform and dried. After dissolving in a mixture of 80 ml ethanol and 20 ml conc. hydrochloric acid, it is stirred for three days at room temperature. The solvent is stripped off and the residue partitioned between chloroform and water. The organic phase is washed out with aqueous sodium carbonate solution and hereafter mixed with ethereal hydrochloric acid solution. After removal of the solvent, the residue is chromatographed on silica gel with chloroform+methanol 10+1 as elution agent. After crystallization of the main fraction from ethanol/ether, one obtains 1.4 g colorless crystals of mp 184° C.

Variant B:

To a solution of 16.0 g 2-ethylthio-5-oxo-4,4-diphenyl-2-pyrrolin-3-carbonitril in 250 ml dimethylsulfoxide there are added 1.5 g sodium hydride (80% in white oil). After 15 minutes of stirring there is added dropwise a solution of 13.1 g 3-(tert.-butoxycarbonylamino)-1-propylbromide in 10 ml anhydrous dimethylsulfoxide. The reaction mixture is stirred for 16 hours at ambient temperature and thereafter again for six hours at 70° C. The solvent is then removed in a vacuum and the remaining residue subjected to chromatography on silica gel using chloroform as eluting agent.

After crystallizing the main fraction from ethylacetate/n-hexane there are obtained 10.6 g 1-(3-tert.-butoxycarbonylaminopropyl)-2-ethylthio-5-oxo-4,4-diphenyl-2-pyrrolin-3-carbonitril of mp 88° C.

9.5 g of the latter compound are then suspended in 20 ml ethanol saturated with hydrogen chloride. The mixture is then stirred for 50 minutes at ambient temperature. The suspended compound is slowly dissolved and later on a precipitate is formed, which is sucked off after dilution with diethylether.

After crystallization from ethanol there are obtained 5.7 g 1-(3-aminopropyl)-2-ethylthio-5-oxo-4,4-diphenyl-2-pyrrolin-3-carbonitril of mp 185° C.

EXAMPLE 6

1-(3-Ethylaminopropyl)-2-ethylthio-5-oxo-4,4-diphenyl-2-pyrroline-3-carbonitrile hydrochloride (17b)

8.8 g 1-(3-bromopropyl)-2-ethylthio-5-oxo-4,4-diphenyl-2-pyrroline-3-carbonitrile and 3.0 g ethylamine are stirred for two days at room temperature in 300 ml dioxan. The solvent is removed on a Rotavapor and the residue partitioned between chloroform and dil. sodium bicarbonate solution. The organic phase is evaporated and the residue chromatographed on silica gel with toluene/ethanol 10+1 as elution agent. The base so obtained is converted in ethanolic solution into the corresponding hydrochloride by mixing with ethereal hydrochloric acid solution. One obtains 1.0 g of colorless crystals of mp 173°–174° C., decomp.

EXAMPLE 7

4-(4-Dimethylaminophenyl)-1-(3-dimethylaminopropyl)-2-methylthio-5-oxo-4-(3-pyridyl)-2-pyrroline-3-carbonitrile (21)

A suspension of 3.5 g 4-(4-dimethylaminophenyl)-2-methylthio-5-oxo-4-(3-pyridyl)-2-pyrroline-3-carbonitrile and 0.3 g sodium hydride (80% in white oil) is refluxed for one hour. One then adds dropwise thereto, within ten minutes, a solution of 1.3 g 3-dimethylaminopropyl chloride in 25 ml abs. dioxan and further boils for six hours. After cooling, the reaction mixture is filtered, the solvent is removed on a Rotavapor and the residue is chromatographed on silica gel with chloroform+methanol 10+1 as elution agent. After crystallization of the main fraction from isopropanol, one obtains 1.8 g of colorless crystals of mp 90°–91° C.

Investigation of the Acute Toxicity Method:

The determination of the acute toxicity was carried out on male mice (NMRI) with a body weight of 18 to 23 g. All experimental animals were fasted for 20 hours before commencement of the investigation. Water was available ad libitum. Four animals belonged to each dosage group. The dosage sequence was logarithmic. The test substances were administered either in the form of aqueous solutions or as suspensions in 0.8% Methocel. The administered volumes amounted, in the case of subcutaneous administration, to 10 ml/kg body weight, in the case of intragastral administration to 20 ml/kg body weight. The animals were observed for a total of seven days.

Results:
Acute Toxicity in Mice - Seven Day Values

| Compound No. | Mode of Administration | $LD_{50}$ mg/kg |
|---|---|---|
| 1 | intragastrally | 1600 |
| 5 | intragastrally | >1600 |
| 6 | intragastrally | 1200 |

-continued

| Results: Acute Toxicity in Mice - Seven Day Values | | |
|---|---|---|
| Compound No. | Mode of Administration | LD$_{50}$ mg/kg |
| 8 | intragastrally | 1400 |
| 12 | intragastrally | >1600 |
| 15 | intragastrally | 700 |
| 21 | intragastrally | 1200 |

Collagen-Induced Thrombocyte Aggregation In Vitro (Rats) Method:

The test was carried out according to the method of BORN (Nature, 194, 927-929, 1962). As blood donors, there served male Sprague-Dawley SIV 50 rats with a body weight of 200 g. The blood sampling took place, under ether narcosis, from the retroorbital venous complex. Nine parts of blood were mixed with one part of 3.8% w/v tri-Na-citrate solution. After low speed centrifuging of the mixture at room temperature, the platelet-rich plasma (PRP, corresponding to erythrocyte-free supernatant) was removed and adjusted to a standard concentration of 4000,000 μl. As measurement instrument, there served an universal aggregometer (Braun, Melsungen), coupled with an Eppendorf photometer 1100M (Netheler and Hinz, Hamburg). In the investigation, 700 μl amounts of PRP were equilibrated in the aggregometer for five minutes at 37° C. and then mixed with 58 μl of the test substance solution or of a 0.9% NaCl solution (corresponding to the blank). After an incubation time of three minutes, the addition of 35 μl collagen suspension (collagen reagent HORM ®, Hormon Chemie, München) initiated the aggregation. A compensation recorder registered, in the following 15 minutes, the change of the transmission.

The largest change of the transmission occurring in the period of time was called the amplitude (Amp) of the aggregation curve. Aggregation-inhibiting substances bring about a reduction of this amplitude; the inhibitory action (E) of a substance is calculated according to the following formula:

$$E = [(Amp)_{blank} - AMP_{test\ subst.}]/Amp_{blank} \times 100(\%)$$

Dosage-action curves are produced on the basis of which their C$_{50}$ values could be calculated. The C$_{50}$ value gives the end concentration of a substance in the test system which leads to a lowering of the amplitude by 50%.

| Results: | | |
|---|---|---|
| Compound No. | Number of experiments | C$_{50}$-value (mmol/l) arith. M. + S.D. |
| 3 | 5 | 0.15 ± 0.04 |
| 6 | 5 | 0.19 ± 0.04 |
| 8 | 5 | 0.27 ± 0.05 |
| 12 | 6 | 0.15 ± 0.02 |
| 16 | 6 | 0.14 ± 0.06 |
| 17a | 6 | 0.06 ± 0.00 |
| 21 | 6 | 0.16 ± 0.02 |

The compounds set out in the table show remarkable aggregation-inhibiting properties, compound 17a being the most effective representative.

Investigation of the Antiphlogistic Action on Carrageenin Edema of Rats Method:

Experimental animals were male rats (SIV 50), fasted for 20 hours, with a body weight of 110-160 g. Water was available ad libitum. After determination of the initial value of the paw volume of the right hind extremity, the test substances were administered intragastrally as suspension in 0.8% Methocel. Ten animals were used per dosage. The volume of administration amounted to 20 ml/kg body weight. The paw volume was measured plethysmometrically. Sixty minutes after intragastral administration of the test substances, 0.1 ml of a 1% carrageenin solution was injected subplanatary into the right hind paw.

One and three hours after injection of the carrageenin, the paw volume of the oedematous paw was measured. The increase of the paw volume of the substance-treated animals after three hours was compared with that in the case of the control animals and the inhibition of the paw edema by the test substance was calculated as a percentage thereof.

| Results: Antiphlogistic Action on Carrageenin Edema of the Rat | | |
|---|---|---|
| Compound No. | Dosage mg/kg Intragastrally | Inhibition of Paw Edema in % |
| 1 | 125 | 36 |
| 5 | 37.5/75 | 22/45 |
| 6 | 125 | 36 |
| 15 | 150 | 39 |

Investigation of the Antipyretic Action on Yeast Fever of the Rat Method:

Experimental animals were male rats (SIV 50), fasted for 20 hours, with a body weight of 115-165 g. For the production of an elevated body temperature, the animals received, 18 hours before administration of the test substances, 20 ml/kg body of a 12% dry yeast suspension subcutaneously in two to three depots. A control group received the corresponding volume of physiological NaCl solution injected subcutaneously. Ten animals were used per dosage. After three preliminary measurementds of the body temperature on the experimental day in 30-minute intervals, the test substance was administered intragastrally to the animals treated with yeast. The volume of administration amounted to 20 ml/kg body weight. A second control group treated with yeast, as well as the control group treated the previous day with physiological NaCl solution, received the corresponding vehicle instead of test substance. The body temperature of the experimental animals was measured rectally by means of thermocouple sensor 30, 60 minutes and then, in each case, hourly up to a total of five hours after substance administration.

| Results: Antipyretic Action on Yeast Fever of the Rat | | | | | | |
|---|---|---|---|---|---|---|
| Substance | 30 | 60 | 120 | 180 | 240 | 300 |
| NaCl 20 ml/kg SC. Methocel 20 ml/kg IG | 36.9 | 36.7 | 36.7 | 36.6 | 36.6 | 36.7 |
| 12% yeast 20 ml/kg SC Methocel 20 ml/kg IG | 38.3 | 38.2 | 38.3 | 38.1 | 38.0 | 37.8 |
| 12% yeast 20 ml/kg SC Go 4775 250 mg/kg IG Compd. No. 6 | 37.0 | 36.0 | 35.2 | 34.7 | 35.1 | 35.6 |
| NaCl 20 ml/kg SC. | — | 36.8 | 36.9 | 36.9 | 36.9 | 37.0 |

-continued

Results:
Antipyretic Action on Yeast Fever of the Rat

| Substance | 30 | 60 | 120 | 180 | 240 | 300 |
|---|---|---|---|---|---|---|
| Methocel 20 ml/kg IG 12% yeast 20 ml/kg SC | — | 38.6 | 38.6 | 38.5 | 38.5 | 38.6 |
| Methocel 20 ml/kg IG 12% yeast 20 ml/kg SC 150 mg/kg IG Compd. No. 15 | — | 36.6 | 35.8 | 35.9 | 36.4 | 37.0 |

The stated compounds show a marked antipyretic action, it resulting in a lowering of the body temperature below the values of animals without yeast fever.

Investigation of the Ulcer-Protective Action on Stomach Ulcer of the Rat Induced by Indomethacin.

Method:

Experimental animals were male rats (SIV 50), fasted for 20 hours, with a body weight of 150–200 g. Water was available ad libitum. 40 mg/kg indomethacin and the substance to be tested, as suspension in 0.8% Methocel, were simultaneously administered to the animals intragastrally. The control animals only received the corresponding dosage of indomethacin. Ten animals were used per experimental group. The administration volume amount to 10 ml/kg body weight. The animals were sacrificed five hours after administration. After removal of the stomachs and opening of the curvatura major, these were investigated with a stereo magnifying glass for the presence of ulcers. The assessment of the ulcers took place according to a point scheme proposed by M. Chaumontet et al. (Arzneim.-Forsch., 28, 2119, 1978). The ulcer index was calculated herefrom. The ulcer index of the animals treated with indomethacin and test substance was compared with that of the control animals only treated with indomethacin and the ulcer inhibition calculated therefrom in percent.

Results:
Ulcer-Protective Action on Stomach Ulcer of the Rat Induced by Indomethacin

| Compound No. | Dosage mg/kg Intragastrally | Ulcer Inhibition in % |
|---|---|---|
| 5 | 100 | 52 |
| 9 | 250 | 29 |
| 15 | 150 | 29 |

With regard to ulcer-protective action, Comp. No. 5 is the most effective representative and, at the same time, the compound with the most favorable therapeutic quotients.

We claim:

1. A compound of the formula

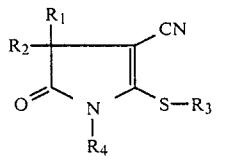

in which $R_1$ and $R_2$ are the same or different and signify an optionally substituted aromatic ring, $R_3$ signifies a straight or branched chain hydrocarbon radical of one to four carbon atoms, $R_4$ signifies an aminoalkyl group of the formula

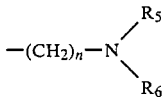

in which n is equal to two or three and $R_5$ and $R_6$ are the same or different and individually signify hydrogen, a straight or branched chain alkyl group of one to four carbon atoms or, together with the nitrogen atom to which they are attached, a ring with possibly further heteroatoms or a pharmaceutically acceptable acid-addition salt thereof.

2. A compound according to claim 1, in which $R_1$ and $R_2$ signify a phenyl, a dimethylaminophenyl or a pyridyl ring, $R_3$ signifies a straight or branched chain $C_{1-3}$ alkyl group and $R_4$ signifies an aminoalkyl group of the formula

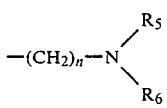

in which n is equal to two or three, and $R_5$ and $R_6$ are the same or different and signify hydrogen, a methyl, ethyl, propyl or isopropyl radical or, together with the nitrogen atom to which they are attached, signify a pyrrolidino, piperidino, morpholino or piperazino group, or a pharmaceuticaaly acceptable salt thereof.

3. A compound according to claim 1 and being 2-ethylthio-5-oxo-4,4-diphenyl-1-(2-piperidinoethyl)-2-pyrroline-3-carbonitrile hydrochloride.

4. A compound according to claim 1 and being 2-ethylthio-1-(3-dimethylaminopropyl)-5-oxo-4,4-diphenyl-2-pyrroline-3-carbonitrile hydrochloride.

5. A compound according to claim 1 and being 2-ethylthio-1-(3-morpholinopropyl)-5-oxo-4,4-diphenyl-2-pyrroline-3-carbonitrile.

6. A compound according to claim 1 and being 1-(2-dimethylaminopropyl)-2-methylthio-5-oxo-4,4-diphenyl-2-pyrroline-3-carbonitrile.

7. A compound according to claim 1 and being 2-isopropylthio-1-(3-dimethylaminopropyl)-5-oxo-4,4-diphenyl-2-pyrroline-3-carbonitrile.

8. A compound according to claim 1 and being 2-methylthio-5-oxo-4,4-diphenyl-1-(3-piperidinopropyl)-2-pyrroline-3-carbonitrile.

9. A compound according to claim 1 and being 1-(2-diethylaminoethyl)-5-oxo-4,4-diphenyl-2-propylthio-2-pyrroline-3-carbonitrile.

10. A compound according to claim 1 and being 2-ethylthio-5-oxo-4,4-diphenyl-1-(3-piperidinopropyl)-2-pyrroline-3-carbonitrile oxalate.

11. A compound according to claim 1 and being 1-(3-diethylaminopropyl)-2-ethylthio-5-oxo-4,4-diphenyl-2-pyrroline-3-carbonitrile hydrochloride.

12. A compound according to claim 1 and being 1-(3-aminopropyl)-2-ethylthio-5-oxo-4,4-diphenyl-2-pyrroline-3-carbonitrile hydrochloride.

13. A compound according to claim 1 and being 4-(4-dimethylaminophenyl)-1-(3-dimethylaminopropyl)-2-methylthio-5-oxo-4-(3-pyridyl)-2-pyrroline-3-carbonitrile.

14. A pharmaceutical composition for the prophylaxis and therapy of thrombotic states comprising an effective amount of a compound according to claim 1 together with a pharmaceutically acceptable carrier.

15. A method for the prophylaxis and therapy of thrombotic states comprising administering to a subject in need thereof an effective amount of a composition according to claim 14.

* * * * *